United States Patent
Knutson et al.

(10) Patent No.: US 10,948,480 B2
(45) Date of Patent: *Mar. 16, 2021

(54) IMMUNITY TO FOLATE RECEPTORS

(71) Applicant: Mayo Foundation for Medical Education and Research, Rochester, MN (US)

(72) Inventors: Keith L. Knutson, Jacksonville, FL (US); Lynn C. Hartmann, Rochester, MN (US); Kimberly R. Kalli, Dover, MN (US); Christopher J. Krco, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 142 days.

This patent is subject to a terminal disclaimer.

(21) Appl. No.: 15/918,777

(22) Filed: Mar. 12, 2018

(65) Prior Publication Data

US 2018/0231521 A1 Aug. 16, 2018

Related U.S. Application Data

(60) Continuation of application No. 14/969,289, filed on Dec. 15, 2015, now Pat. No. 9,915,646, which is a continuation of application No. 13/917,410, filed on Jun. 13, 2013, now Pat. No. 9,243,033, which is a division of application No. 12/303,054, filed as application No. PCT/US2007/070237 on Jun. 1, 2007, now Pat. No. 8,486,412.

(60) Provisional application No. 60/810,242, filed on Jun. 1, 2006.

(51) Int. Cl.
| | |
|---|---|
| *C07K 14/435* | (2006.01) |
| *G01N 33/50* | (2006.01) |
| *C07K 14/47* | (2006.01) |
| *C07K 14/705* | (2006.01) |
| *A61K 39/00* | (2006.01) |
| *C07K 7/08* | (2006.01) |
| *A61K 38/04* | (2006.01) |

(52) U.S. Cl.
CPC .... *G01N 33/505* (2013.01); *A61K 39/001102* (2018.08); *C07K 7/08* (2013.01); *C07K 14/4748* (2013.01); *C07K 14/705* (2013.01); *A61K 38/04* (2013.01); *A61K 39/0011* (2013.01); *G01N 2333/705* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,547,668 A | 8/1996 | Kranz et al. |
| 7,033,594 B2 | 4/2006 | Low et al. |
| 7,547,759 B2 | 6/2009 | Ioannides et al. |
| 8,486,412 B2 | 7/2013 | Knutson |
| 9,243,033 B2 | 1/2016 | Knutson |
| 2001/0008625 A1 | 7/2001 | Larsen et al. |

FOREIGN PATENT DOCUMENTS

WO  WO 2004/047871  6/2004

OTHER PUBLICATIONS

Zaro (2015) AAPS Journal 17: 83-92.*
Bagnoli et al., "A step further in understanding the biology of the folate receptor in ovarian carcinoma," *Gynecol. Oncol.*, 2003, 88(1 Pt 2):S140-S144.
Bottero et al., "Gene Transfection and Expression of the Ovarian Carcinoma Marker Folate Binding Protein on NIH/3T3 Cells Increases Cell Growth in Vitro and in Vivo," *Cancer Res.*, 1993, 53:5791-5796.
Campbell et al., "Folate-binding Protein Is a Marker for Ovarian Cancer," *Cancer Res.*, 1991, 51:5329-5338.
Da Costa et al., "Antibodies to folate receptors impair embryogenesis and fetal development in the rat," *Res. A. Clin. Mol. Teratol.*, 2003, 67:837-847.
Disis et al., "Maximizing the retention of antigen specific lymphocyte function after cryopreservation," *J. Immunol. Methods*, 2006, 308(1-2):13-18.
Elnakat and Ratnam, "Distribution, functionality and gene regulation of folate receptor isoforms: implications in targeted therapy," *Adv. Drug Deliv. Rev.*, 2004, 56:1067-1084.
GenBank® Accession No. NM_016725, "Homo sapiens folate receptor 1 (adult) (FOLR1), transcript variant 1, mRNA," May 10, 2009, 5 pages.
Holm et al., "Folate receptor of human mammary adenocarcinoma," *Apmis*, 1994, 102:413-419.
Holm et al., "High-affinity folate binding in human mammary gland," *Biosci. Rep.*, 1993, 13:1-7.
Holm et al., "The high-affinity folate binding protein in normal and malignant mammary gland tissue," *Adv. Exp. Med. Biol.*, 1993, 338:757-760.
Kim et al., "The comparison of cytotoxic T-lymphocyte effects of dendritic cells stimulated by the folate binding protein peptide cultured with IL-15 and IL-2 in solid tumor," *Yonsei Med J.*, 2002, 43(6):691-700.

(Continued)

*Primary Examiner* — Michael D Pak
(74) *Attorney, Agent, or Firm* — Fish & Richardson P.C.

(57) ABSTRACT

This document provides methods and materials related to assessing immunity to folate receptors. For example, methods and materials for assessing FRα immunity in a mammal are provided. This document also provides methods and materials related to stimulating immunity to folate receptors.

5 Claims, 9 Drawing Sheets

Specification includes a Sequence Listing.

(56) References Cited

OTHER PUBLICATIONS

Knutson and Disis, "Tumor antigen-specific T helper cells in cancer immunity and immunotherapy," *Cancer Immunol. Immunother.*, 2005, 54:721-728.

Knutson et al., "Immunization with a HER-2/neu helper peptide vaccine generates HER-2/neu CD8 T-cell immunity in cancer patients," *J. Clin. Invest.*, 2001, 107:477-484.

Knutson et al., "T-cell immunity to the folate receptor alpha is prevalent in women with breast or ovarian cancer," *Journal of Clinical Oncology*, 2006, 24(26):4254-4261.

Lu et al., "Folate receptor-targeted immunotherapy of cancer: mechanism and therapeutic potential," Adv *Drug Deliv Rev.*, 2004, 56(8):1161-76.

Lu et al., "Immunotherapy of folate receptor-expressing tumors: review of recent advances and future prospects," *Journal of Controlled Release*, 2003, 91(1-2):17-29.

Parker et al., "Folate receptor expression in carcinomas and normal tissues determined by a quantitative radioligand binding assay," *Anal. Biochem.*, 2005, 338:284-293.

Peoples et al., "Vaccine implications of folate binding protein, a novel cytotoxic T lymphocyte-recognized antigen system in epithelial cancers," *Clin Cancer Res.*, 1999, 5(12):4214-4223.

Peoples et al., Ovarian cancer-associated lymphocytes recognize folate binding protein (FBP) peptides, *Annals of Surgical Oncology*, 1998, 5(8):743-750.

Ramaekers and Blau, "Cerebral folate deficiency," *Dev. Med. Child Neurol.*, 2004, 46:843-851.

Ramaekers et al., "Autoantibodies to Folate Receptors in the Cerebral Folate Deficiency Syndrome," *N. Engl. J. Med.*, 2005, 352:1985-1991.

Ramakrishna et al. "Generation and phenotypic characterization of new human ovarian cancer cell lines with the identification of antigens potentially recognizable by HLA-restricted cytotoxic T cells," *Int J Cancer.*, 1997, 73(1):143-150.

Rothenberg et al., "Autoantibodies against Folate Receptors in Women with a Pregnancy Complicated by a Neural-Tube Defect," *N. Engl. J. Med.*, 2004, 350:134-142.

Schwartz, "Autoimmune Folate Deficiency and the Rise and Fall of 'Horror Autotoxicus'," *N. Engl. J. Med.*, 2005, 352:1948-1950.

Toffoli et al., "Expression of folate binding protein as a prognostic factor for response to platinum-containing chemotherapy and survival in human ovarian cancer," *Int. J. Cancer*, 1998, 79:121-126.

Toffoli et al., "Overexpression of folate binding protein in ovarian cancers," *Int. J. Cancer*, 1997, 74:193-198.

Weitman et al., "Distribution of the folate receptor GP38 in normal and malignant cell lines and tissues," *Cancer Res.*, 1992, 52:3396-3401.

Willemsen et al., "Cerebral folate deficiency syndrome," *N. Engl. J. Med.* 2005, 353:740.

International Preliminary Report on Patentability in PCT/US2007/070237, dated Dec. 18, 2008, 9 pages.

International Search Report and Written Opinion for PCT/US2007/070237, dated Oct. 15, 2007, 17 pages.

Volpina, O.M., et al., Vaccine, 14(14): 1375-1380, 1996.

\* cited by examiner

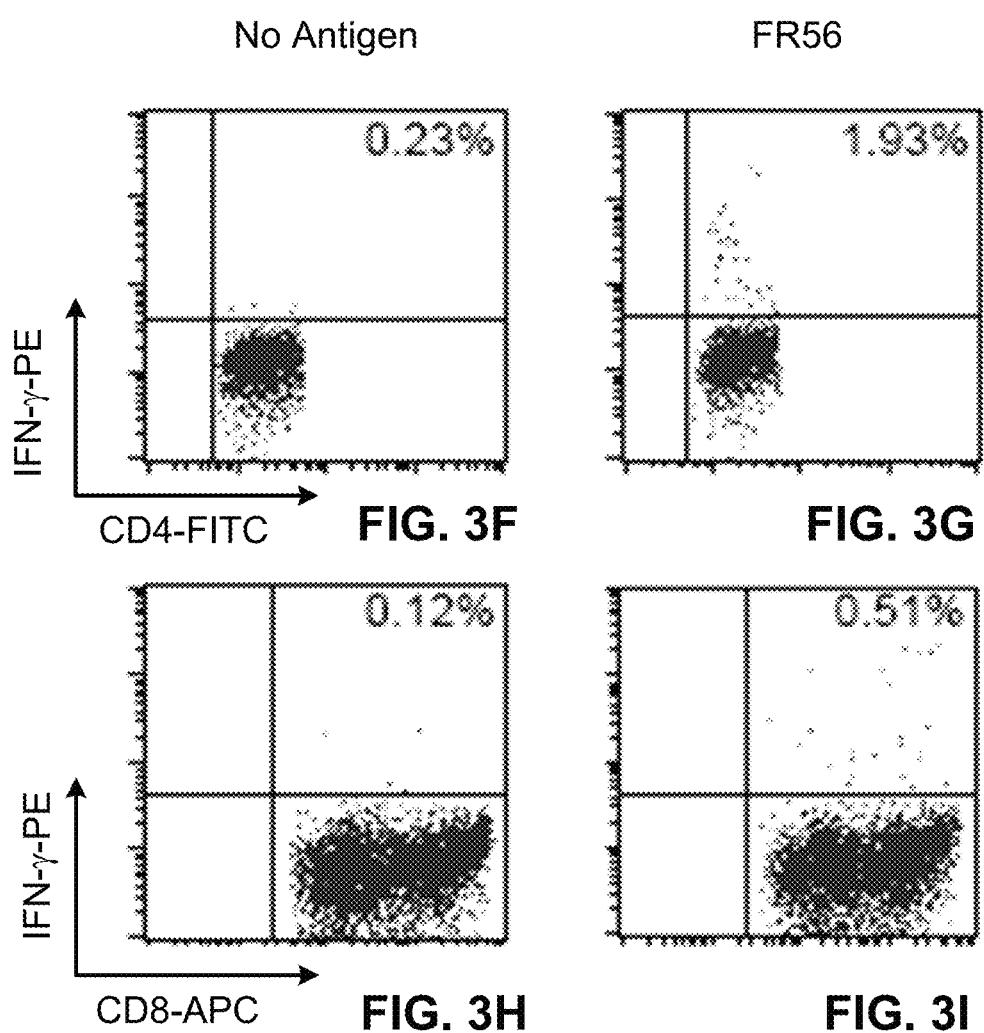

SEQUENCE LISTING

```
<160> NUMBER OF SEQ ID NOS: 16

<210> SEQ ID NO 1
<211> LENGTH: 17
<212> TYPE: PRT
<213> ORGANISM: Gallus gallus

<400> SEQUENCE: 1

Lys Ile Ser Gln Ala Val His Ala Ala His Ala Glu Ile Asn Glu Ala
1               5                   10                  15

Gly

<210> SEQ ID NO 2
<211> LENGTH: 19
<212> TYPE: PRT
<213> ORGANISM: Homo sapiens

<400> SEQUENCE: 2
```

```
Met Thr Thr Gln Leu Leu Leu Leu Val Trp Val Ala Val Val Gly
1               5                   10                  15

Glu Ala Gln

<210> SEQ ID NO 3
<211> LENGTH: 15
<212> TYPE: PRT
<213> ORGANISM: Homo sapiens

<400> SEQUENCE: 3

Leu Leu Val Trp Val Ala Val Val Gly Glu Ala Gln Thr Arg Ile
1               5                   10                  15

<210> SEQ ID NO 4
<211> LENGTH: 17
<212> TYPE: PRT
<213> ORGANISM: Homo sapiens

<400> SEQUENCE: 4

Arg Thr Glu Leu Leu Asn Val Cys Met Asn Ala Lys His His Lys Glu
1               5                   10                  15

Lys

<210> SEQ ID NO 5
<211> LENGTH: 15
<212> TYPE: PRT
<213> ORGANISM: Homo sapiens

<400> SEQUENCE: 5

Gln Cys Arg Pro Trp Arg Lys Asn Ala Cys Cys Ser Thr Asn Thr
1               5                   10                  15

<210> SEQ ID NO 6
<211> LENGTH: 18
<212> TYPE: PRT
<213> ORGANISM: Homo sapiens

<400> SEQUENCE: 6

Lys Asp Val Ser Tyr Leu Tyr Arg Phe Asn Trp Asn His Cys Gly Glu
1               5                   10                  15

Met Ala

<210> SEQ ID NO 7
<211> LENGTH: 16
<212> TYPE: PRT
<213> ORGANISM: Homo sapiens

<400> SEQUENCE: 7

Ala Cys Lys Arg His Phe Ile Gln Asp Thr Cys Leu Tyr Glu Cys Ser
1               5                   10                  15

<210> SEQ ID NO 8
<211> LENGTH: 17
<212> TYPE: PRT
<213> ORGANISM: Homo sapiens

<400> SEQUENCE: 8

Leu Gly Pro Trp Ile Gln Gln Val Asp Gln Ser Trp Arg Lys Glu Arg
1               5                   10                  15

Val

<210> SEQ ID NO 9
```

```
<211> LENGTH: 15
<212> TYPE: PRT
<213> ORGANISM: Homo sapiens

<400> SEQUENCE: 9

Val Asp Gln Ser Trp Arg Lys Glu Arg Val Leu Asn Val Pro Leu
1               5                   10                  15

<210> SEQ ID NO 10
<211> LENGTH: 16
<212> TYPE: PRT
<213> ORGANISM: Homo sapiens

<400> SEQUENCE: 10

Asp Cys Glu Gln Trp Trp Glu Asp Cys Arg Thr Ser Tyr Thr Cys Lys
1               5                   10                  15

<210> SEQ ID NO 11
<211> LENGTH: 17
<212> TYPE: PRT
<213> ORGANISM: Homo sapiens

<400> SEQUENCE: 11

Arg Thr Ser Tyr Thr Cys Lys Ser Asn Trp His Lys Gly Trp Asn Trp
1               5                   10                  15

Thr

<210> SEQ ID NO 12
<211> LENGTH: 16
<212> TYPE: PRT
<213> ORGANISM: Homo sapiens

<400> SEQUENCE: 12

Cys Lys Ser Asn Trp His Lys Gly Trp Asn Trp Thr Ser Gly Phe Asn
1               5                   10                  15

<210> SEQ ID NO 13
<211> LENGTH: 18
<212> TYPE: PRT
<213> ORGANISM: Homo sapiens

<400> SEQUENCE: 13

Trp His Lys Gly Trp Asn Trp Thr Ser Gly Phe Asn Lys Cys Ala Val
1               5                   10                  15

Gly Ala

<210> SEQ ID NO 14
<211> LENGTH: 16
<212> TYPE: PRT
<213> ORGANISM: Homo sapiens

<400> SEQUENCE: 14

Val Ala Arg Phe Tyr Ala Ala Ala Met Ser Gly Ala Gly Pro Trp Ala
1               5                   10                  15

<210> SEQ ID NO 15
<211> LENGTH: 18
<212> TYPE: PRT
<213> ORGANISM: Homo sapiens

<400> SEQUENCE: 15

Pro Trp Ala Ala Trp Pro Phe Leu Leu Ser Leu Ala Leu Met Leu Leu
1               5                   10                  15
```

```
Trp Leu

<210> SEQ ID NO 16
<211> LENGTH: 20
<212> TYPE: PRT
<213> ORGANISM: Homo sapiens

<400> SEQUENCE: 16

Pro Pro Gly Leu Thr Gly Pro Ala Gly Glu Pro Gly Arg Gln Gly Ser
1               5                   10                  15

Pro Gly Ala Asp
            20
```

IMMUNITY TO FOLATE RECEPTORS

CROSS-REFERENCE TO RELATED APPLICATIONS

This application is a continuation of U.S. application Ser. No. 14/969,289 (now U.S. Pat. No. 9,915,646), filed Dec. 15, 2015, which is a continuation of U.S. application Ser. No. 13/917,410 (now U.S. Pat. No. 9,243,033), filed Jun. 13, 2013, which is a divisional of U.S. application Ser. No. 12/303,054 (now U.S. Pat. No. 8,486,412), filed Jul. 13, 2010, which is a National Stage application under 35 U.S.C. § 371 of International Application No. PCT/US2007/070237 having an International Filing Date of Jun. 1, 2007, which claims the benefit of U.S. Provisional Application Ser. No. 60/810,242, filed Jun. 1, 2006. The disclosures of the prior applications are considered part of (and are incorporated by reference in) the disclosure of this application.

STATEMENT AS TO FEDERALLY SPONSORED RESEARCH

This invention was made with government support under CA015083 awarded by the National Institutes of Health. The government has certain rights in the invention.

BACKGROUND

1. Technical Field

This document relates to methods and materials involved in assessing immunity to folate receptors as well as methods and materials involved in stimulating immunity to folate receptors.

2. Background Information

Folate receptor α (FRα) is a GPI-linked protein that is important in neurological development and is overexpressed on nearly all ovarian cancers and a high proportion of breast cancers (Parker et al., *Anal. Biochem.*, 338:284-93 (2005); Bagnoli et al., *Gynecol. Oncol.*, 88:S140-4 (2003); Holm et al., *Apmis*, 102:413-9 (1994); Holm et al., *Biosci. Rep.*, 13:1-7 (1993); Holm et al., *Adv. Exp. Med. Biol.*, 338:757-60 (1993); Weitman et al., *Cancer Res.*, 52:3396-401 (1992); and Elnakat and Ratnam, *Adv. Drug Deliv. Rev.*, 56:1067-84 (2004)). Overexpression of FRα is associated with increased tumor aggressiveness (Toffoli et al., *Int. J. Cancer*, 79:121-6 (1998); Toffoli et al., *Int. J. Cancer*, 74:193-8 (1997); Bottero et al., *Cancer Res.*, 53:5791-6 (1993); and Campbell et al., *Cancer Res.*, 51:5329-38 (1991)). Immunity to FRα is associated with neural tube defects in the developing embryo and cerebral folate deficiency syndrome in children (Rothenberg et al., *N. Engl. J. Med.*, 350:134-42 (2004); da Costa et al., *Res. A. Clin. Mol. Teratol.*, 67:837-47 (2003); Willemsen et al., *N. Engl. J. Med.* 353:740 (2005); Ramaekers et al., *N. Engl. J. Med.*, 352:1985-91 (2005); Schwartz, *N. Engl. J. Med.*, 352:1948-50 (2005); and Ramaekers and Blau, *Dev. Med. Child Neurol.*, 46:843-51 (2004)).

SUMMARY

This document provides methods and materials related to assessing immunity to folate receptors. For example, this document provides compositions containing polypeptides that can be used to assess whether or not a mammal (e.g., a mammal having cancer) has mounted an immune response (e.g., T or B cell response) against a folate receptor polypeptide (e.g., a folate receptor α). Determining whether or not a cancer patient has mounted an immune response against a folate receptor polypeptide can help clinicians assess the patient's prognosis. For example, a cancer patient identified as having mounted an immune response against a folate receptor polypeptide can be categorized as having an improved prognosis as compared to a similar cancer patient who has not mounted an immune response against a folate receptor polypeptide. Such prognostic information can help clinicians and patients select appropriate treatment options. Folate receptor immunity also can be used as a marker for the early detection of cancer. For example, ovarian cancer usually presents as an advanced untreatable disease. The methods and materials provided herein can be used to detect early disease, thereby reducing mortality and morbidity.

This document also provides methods and materials related to stimulating immunity to folate receptors. For example, this document provides compositions containing polypeptides that can be used to stimulate an immune response against a folate receptor polypeptide. Stimulating an anti-folate receptor polypeptide response in a mammal having cancer can improve the mammal's prognosis. For example, a cancer patient receiving a composition provided herein can mount an immune response against a folate receptor polypeptide, thereby reducing the aggressiveness of the cancer.

In general, one aspect of this document features a method for assessing FRα immunity in a mammal having cancer. The method comprises, or consists essentially of, determining whether or not the mammal comprises T cells reactive to an FRα polypeptide selected from the group consisting of FR5, FR12, FR30, FR56, FR76, FR95, FR113, FR120, FR138, FR147, FR152, FR156, FR225, and FR238. The mammal can be a human. The cancer can be breast or ovarian cancer. The FRα polypeptide can be FR30, FR56, FR76, FR113, FR138, or FR147.

In another aspect, this document features a substantially pure polypeptide selected from the group consisting of FR5, FR12, FR30, FR56, FR76, FR95, FR113, FR120, FR138, FR147, FR152, FR156, FR225, and FR238.

In another aspect, this document features a kit comprising, or consisting essentially of, a polypeptide selected from the group consisting of FR5, FR12, FR30, FR56, FR76, FR95, FR113, FR120, FR138, FR147, FR152, FR156, FR225, and FR238. The kit can comprise two or more of the polypeptides.

In another aspect, this document features a method for increasing FRα immunity in a mammal. The method comprises, or consists essentially of, administering a composition to the mammal under conditions effective to increase the FRα immunity, where the composition comprises a polypeptide selected from the group consisting of FR5, FR12, FR30, FR56, FR76, FR95, FR113, FR120, FR138, FR147, FR152, FR156, FR225, and FR238. The mammal can be a human. The composition can comprise an adjuvant.

In another aspect, this document features a method for identifying a mammal as having cancer. The method comprises, or consists essentially of, (a) determining whether or not a mammal contains an elevated level of anti-folate receptor polypeptide antibodies, and (b) classifying the mammal as having cancer when the elevated level is present. The mammal can be human. The cancer can be ovarian or breast cancer. The elevated level of anti-folate receptor polypeptide antibodies can be a level greater than 25 ng/mL, 30 ng/mL, 35 ng/mL, 40 ng/mL, 45 ng/mL, or 50 ng/mL. The anti-folate receptor polypeptide antibodies can be directed against at least one polypeptide selected from the group consisting of FR5, FR12, FR30, FR56, FR76, FR95, FR113, FR120, FR138, FR147, FR152, FR156, FR225, and FR238.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 3A-3L contain graphs and images demonstrating that patients with breast or ovarian cancer can generate immune responses to multiple polypeptide epitopes in an FRα polypeptide. Panel A is a bar graph plotting the mean (±s.e.m.) number of spots per million peripheral blood mononuclear cells (PBMC) for responses to phorbolmyristyl-acetate (PMA)-ionomycin, CEF (cytomegalovirus-EBV-Influenza) peptide pool, or ovalbumin-derived control polypeptide (OVA) in patients and healthy donors. Panels B and C are graphs plotting the T cell frequencies (per million PBMC) for patients and healthy donors, respectively. Each dot represents the mean response of three replicates for an individual specimen. The bars for each polypeptide epitope data set represent the mean T cell frequency observed for that group. Both CD4$^+$ and CD8$^+$ T cells were activated in response to the polypeptide stimulation. Panels D and E contain results of ELIspot analyses for patient 37 and healthy donor 15. Patient 37 demonstrated an FR56-specific response (183±17 spots/well, mean±s.e.m., n=3) which was higher (p=0.0008) than the no antigen (26±2 spots/well) control. The responses to the CEF pool were not significantly elevated compared to control (p>0.5). Donor 15 did not demonstrate elevated FR56-specific T cell (3±1 spots/well, p>0.05) compared to control (5±1 spots/well), but did have an elevated CEF pool response (76±5 spots/well, p=0.0003). PBMC from three patients that had responded to FR56 were examined using IFN-γ cytokine flow cytometry. Analysis of the FR56 polypeptide using the MHCPred MHC class I predicting algorithm suggested this epitope contained high affinity binding epitopes for HLA-A2 and HLA-A3. All three patients demonstrated a CD4 T cell response to the FR56 polypeptide, while two of three demonstrated a CD8 T cell response of which a representative example is shown in FIGS. 3F-I. Panel J is a bar graph plotting the mean (±s.e.m.) number of polypeptide epitopes to which the healthy donors and ovarian or breast cancer patients responded. Panel K is a relational diagram plotting the T cell frequencies in the healthy donor and patient populations. Each set of data points connected by a bar represents a unique polypeptide epitope. Each data point is the mean T cell frequency calculated within each cohort. Panel L shows that the elevated T cell frequencies observed in the patient were mostly confined to the amino terminus. The mean T cell frequency per patient for the amino terminus polypeptides was 75±17 (mean±s.e.m) which, was higher than the frequency observed in healthy donors (24±11, p=0.007). A subsequent analysis revealed that FR76 was a topmost predicted B cell epitope, and this polypeptide was used to monitor for FRα-specific antibodies.

FIG. 4A. Patients demonstrated increased antibody immunity to FRα. Levels of FRα-specific antibodies in patients were 68±6 ng/mL (mean±s.e.m., n=18), which was significantly higher (p<0.0001) than levels in the normal healthy donors (19±8 ng/mL, n=1). FIG. 4B. Antibody responses to TT were equivalent (p=0.3) between the two populations (patients, 30±4 µg/mL; healthy donors 27±4 µg/mL, p=0.3).

DETAILED DESCRIPTION

Figure 1:
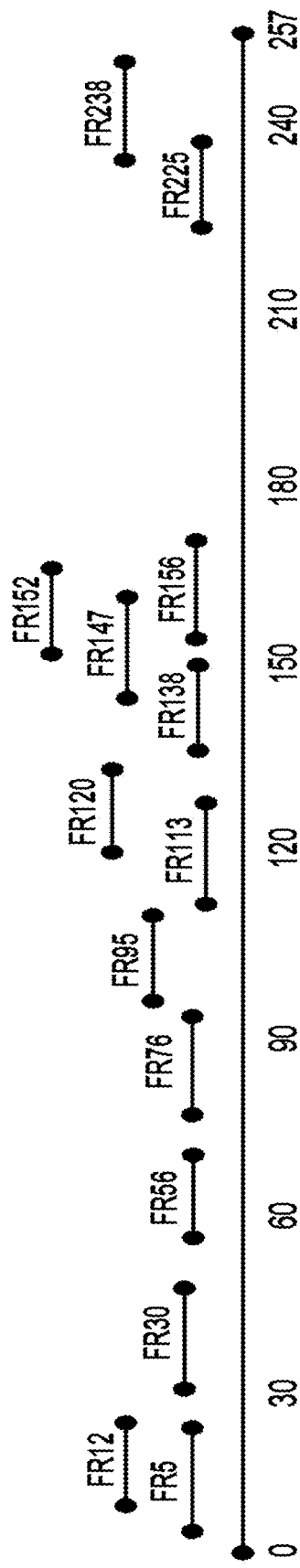
FIG. 1 is a diagram of an FR polypeptide with the distribution of MHC class II epitopes indicated. The bottom line represents the full length FRα polypeptide. The numbers associated with the small lines indicate the polypeptide epitope name. The amino acid sequence of each polypeptide epitope is set forth in Table 1.

This document provides methods and materials related to assessing immunity to folate receptors. For example, this document provides compositions containing polypeptides that can be used to assess whether or not a mammal (e.g., a mammal having cancer) has mounted an immune response (e.g., T or B cell response) against a folate receptor polypeptide (e.g., a folate receptor α). A mammal having cancer that is identified as having mounted an immune response against a folate receptor polypeptide can be categorized as having an improved prognosis as compared to a similar mammal having cancer that has not mounted an immune response against a folate receptor polypeptide.

Immunity to a folate receptor polypeptide can be assessed in any type of mammal. For example, humans, monkeys, cows, horses, dogs, and cats can be assessed for the presence or absence of an immune response to a folate receptor polypeptide. Examples of folate receptor polypeptides include, without limitation, folate receptor α polypeptides. An amino acid sequence for a human folate receptor α polypeptide can be as set forth in GenBank® accession number NM_016725 (gi|9257206).

Any method can be used to assess a mammal for the presence or absence of an immune response to a folate receptor polypeptide. For example, the methods and FRα polypeptides provided herein can be used to determine whether or not a mammal mounted an immune response (e.g., T cell response) against a folate receptor α polypeptide. In some cases, a mammal can be tested for the ability to respond to a panel of FRα polypeptides. Such a panel can contain two, three, four, five, six, seven, eight, nine, ten, or more individual FRα polypeptides. For example, a panel can contain the FRα polypeptides set forth in Table 1. Examples of FRα polypeptides include, without limitation, FR5, FR12, FR30, FR56, FR76, FR95, FR113, FR120, FR138, FR147, FR152, FR156, FR225, and FR238. In some cases, a mammal found to have immunity to two or more (e.g., two, three, four, five, or more) FRα polypeptides within a panel can be classified as having FRα immunity or enhanced FRα immunity, while a mammal found to have immunity to zero or one FRα polypeptide within the panel can be classified as having minimal or no FRα immunity.

This document also provides substantially pure FRα polypeptides. The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure. A substantially pure polypeptide can be at least about 65, 70, 75, 80, 85, 90, 95, or 99 percent pure. Typically, a substantially pure polypeptide will yield a single major band on a non-reducing polyacrylamide gel.

Any method can be used to obtain a substantially pure polypeptide. For example, common polypeptide purification techniques such as affinity chromatography and HPLC as well as polypeptide synthesis techniques can be used. In addition, any material can be used as a source to obtain a substantially pure polypeptide. For example, tissue from wild-type or transgenic animals can be used as a source material. In addition, tissue culture cells engineered to over-express a particular polypeptide of interest can be used to obtain substantially pure polypeptide. Further, a polypeptide can be engineered to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase.

An FRα polypeptide can be obtained recombinantly, synthetically, or commercially. An FRα polypeptide can have a non-naturally occurring sequence or can have a sequence present in any species (e.g., human, rat, or mouse). In some cases, an FRα polypeptide can contain one or more amino acid analogs or other peptidomimetics. The subunits of an FRα polypeptide may be linked by peptide bonds or other bonds such as, for example, ester or ether bonds. An FRα polypeptide can be a full-length FRα polypeptide, a precursor FRα polypeptide, or a fragment of a full-length FRα polypeptide. In some cases, an FRα polypeptide can contain one or more modifications. For example, an FRα polypeptide can be modified to be pegylated or to contain additional amino acid sequences such as an albumin sequence (e.g., a human albumin sequence). In some cases, an FRα polypeptide can be a fusion polypeptide, such as a fusion polypeptide that contains a fragment of an albumin sequence. In some cases, an FRα polypeptide can be covalently attached to oligomers, such as short, amphiphilic oligomers that enable oral administration or improve the pharmacokinetic or pharmacodynamic profile of a conjugated FRα polypeptide. The oligomers can comprise water soluble polyethylene glycol (PEG) and lipid soluble alkyls (short chain fatty acid polymers). See, for example, International Patent Application Publication No. WO 2004/047871. In some cases, an FRα polypeptide can be fused to the Fc domain of an immunoglobulin molecule (e.g., an IgG1 molecule) such that active transport of the fusion polypeptide occurs across epithelial cell barriers via the Fc receptor. In some cases, an FRα polypeptide can be a fusion polypeptide, such as a fusion polypeptide that contains an FRα polypeptide fused to an immunogenic polypeptide. In some cases, an FRα polypeptide can be designed to contain foreign T-cell epitopes so that administration of the polypeptide to a mammal produces or increases immunity to a folate receptor polypeptide in the mammal.

Any method can be used to obtain a folate receptor polypeptide (e.g., an FRα polypeptide). For example, molecular cloning techniques can be used to prepare a nucleic acid construct encoding a folate receptor polypeptide. Such a construct can be expressed in an organism such as *E. coli* or *S. cerevisiae*, or in a cell line, for example, and the expressed polypeptide can be purified from cellular extracts or from culture supernatants. A folate receptor polypeptide also can be chemically synthesized.

This document also provides methods and materials for increasing a mammal's immunity to a folate receptor polypeptide. For example, one or more of the FRα polypeptides provided herein can be formulated into a composition that can be administered to a mammal (e.g., a mouse, a rat, a cat, a dog, a horse, a cow, a non-human primate such as a cynomolgus monkey, or a human) under conditions that lead to increased immunity against an FRα polypeptide. Such composition can include ingredients found in vaccines such as adjuvants. For example, a composition provided herein can contain one or more FRα polypeptides in combination with an adjuvant (e.g., aluminum hydroxide, aluminum phosphate, calcium phosphate, monophosphoryl lipid A, an ISCOM with Quil-A, or a Syntex adjuvant formulations (SAF)® containing a threonyl derivative or muramyl dipeptide). In some cases, an FRα polypeptide can contain a sequence capable of generating a $CD4^+$ T cell response, a $CD8^+$ T cell response, or both.

Alum as well as other aluminum-based compounds (e.g., $Al_2O_3$) can be combined with a folate receptor polypeptide (e.g., an FRα polypeptide) to form a composition that elicits an immune response against a folate receptor polypeptide (e.g., an FRα polypeptide) when administered to a mammal. Aluminum-based compounds can be obtained from various commercial suppliers. For example, REHYDRAGEL® adjuvants can be obtained from Reheis Inc. (Berkeley Heights, N.J.). REHYDRAGEL® adjuvants are based on crystalline aluminum oxyhydroxide, and are hydrated gels containing crystalline particles with a large surface area (about 525 $m^2/g$). Their $Al_2O_3$ content typically ranges from about 2 percent to about 10 percent. Rehydragel LG, for example, has an $Al_2O_3$ content of about 6 percent, and flows readily upon slight agitation. Rehydragel LG also has a protein binding capacity of 1.58 (e.g., 1.58 mg of bovine serum albumin bound per 1 mg of $Al_2O_3$), a sodium content of 0.02 percent, a chloride content of 0.28 percent, undetectable sulphate, an arsenic level less than 3 ppm, a heavy metal content less than 15 ppm, a pH of 6.5, and a viscosity of 1090 cp. Rehydragel LG can be combined with a polypeptide solution (e.g., a polypeptide in PBS) to yield $Al(OH)_3$. In addition, ALHYDROGEL™, an aluminum hydroxy gel adjuvant, (Alhydrogel 1.3%, Alhydrogel 2.0%, or Alhydrogel "85") obtained from Brenntag Stinnes Logistics can be used.

MN51 also can be combined with a folate receptor polypeptide (e.g., an FRα polypeptide) to form a composition that elicits an immune response against a folate receptor polypeptide (e.g., an FRα polypeptide) when administered to a mammal. MN51 (MONTANIDE® Incomplete SEPPIC Adjuvant (ISA) 51) can be obtained from Seppic (Paris, France). Other adjuvants include immuno-stimulating complexes (ISCOMs) that can contain such components as cholesterol and saponins. Adjuvants such as FCA, FIA, MN51, MN720, and Al(OH)$_3$ are commercially available from companies such as Seppic, Difco Laboratories (Detroit, Mich.), and Superfos Biosector A/S (Vedbeak, Demark).

In some cases, a composition provided herein can contain one or more additional immunostimulatory components. These include, without limitation, muramyldipeptide (e.g., N-acetylmuramyl-L-alanyl-D-isoglutamine; MDP), monophosphoryl-lipid A (MPL), and formyl-methionine containing tripeptides such as N-formyl-Met-Leu-Phe. Such compounds are commercially available from Sigma Chemical Co. (St. Louis, Mo.) and RIBI ImmunoChem Research, Inc. (Hamilton, Mont.), for example.

A "unit dose" of a composition refers to the amount of a composition administered to a mammal at one time. A unit dose of the compositions provided herein can contain any amount of polypeptide. For example, a unit dose of a composition can contain between about 10 μg and about 1 g (e.g., 10 μg, 15 μg, 25 μg, 30 μg, 50 μg, 100 μg, 250 μg, 280 μg, 300 μg, 500 μg, 750 μg, 1 mg, 10 mg, 15 mg, 25 mg, 30 mg, 50 mg, 100 mg, 250 mg, 280 mg, 300 mg, 500 mg, 750 mg, or more) of a polypeptide. In some embodiments, the polypeptide can be dissolved or suspended in a physiological buffer such as, for example, water or phosphate buffered saline (PBS), pH 7.0. The solution of polypeptide then can be combined with the adjuvant and any other components of the composition.

Similarly, a unit dose of a composition can contain any amount of an adjuvant. For example, a unit dose can contain between about 10 μL and about 1 mL (e.g., 10 μL, 25 μL, 50 μL, 100 μL, 250 μL, 500 μL, 750 μL, 800 μL, 900 μL, or 1 mL) of one or more adjuvants. In addition, a unit dose of a composition can contain any amount of another immunostimulatory component. For example, a composition provided herein can contain between about 10 μg and about 1 g (e.g., 10 μg, 15 μg, 25 μg, 30 μg, 50 μg, 100 μg, 250 μg, 280 μg, 300 μg, 500 μg, 750 μg, 1 mg, 10 mg, 15 mg, 25 mg, 30 mg, 50 mg, 100 mg, 250 mg, 280 mg, 300 mg, 500 mg, 750 mg, or more) of an immunostimulatory component.

The compositions provided herein can contain any ratio of adjuvant to polypeptide. The adjuvant:antigen ratio can be 50:50 (vol:vol), for example. Alternatively, the adjuvant:antigen ratio can be, without limitation, 90:10, 80:20, 70:30, 64:36, 60:40, 55:45, 40:60, 30:70, 20:80, or 90:10.

This document also provides methods for preparing the compositions provided herein. Such methods can involve suspending an amount of a polypeptide (e.g., 100 μg of an FRα polypeptide) in a suitable amount of a physiological buffer (e.g., 50 μL of PBS pH 7.0), and then combining the suspended or dissolved polypeptide with a suitable amount of an adjuvant (e.g., 50 μL of MN51 or 100 μL of REHYDRAGEL®). The combining step can be achieved by any method, including stirring, shaking, vortexing, or passing back and forth through a needle attached to a syringe, for example. It is noted that the composition can be prepared in batch such that enough unit doses are obtained for multiple injections (e.g., injections into multiple mammals or multiple injections into the same mammal).

In general, compositions containing an FRα polypeptide can be used as a vaccine to induce or increase immunity against a folate receptor polypeptide (e.g., an endogenous FRα polypeptide) in a mammal (e.g., a mammal having cancer). As described herein, administering a composition comprising an FRα polypeptide to a mammal having cancer can induce or increase an immune response (e.g., a T cell response) against a folate receptor polypeptide in the mammal, which, in turn, can reduce the aggressiveness of a cancer in the mammal and improve the mammal's prognosis. In some cases, administering a composition comprising an FRα polypeptide to a mammal that is susceptible to developing cancer (e.g., a mammal that has a family history of cancer) can induce or increase an immune response against a folate receptor polypeptide in the mammal which, in turn, can delay or prevent the onset of cancer or reduce the aggressiveness of a cancer that develops in the mammal.

The compositions provided herein can be administered by a number of methods. Administration can be, for example, topical (e.g., transdermal, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations).

Any dose can be administered to a mammal. Dosages can vary depending on the relative potency of individual compositions, and can generally be estimated based on data obtained from in vitro and in vivo animal models. Typically, a dosage is from about 0.01 μg to about 100 g per kg of body weight, and may be given once or more daily, weekly, monthly, yearly, or less often. Following successful administration, it may be desirable to have the subject undergo additional booster administrations to maintain a suitable level of the immune response.

The immune response to a folate receptor polypeptide produced in a mammal by administration of a composition provided herein can be assessed using any appropriate method. For example, the titer of anti-folate receptor antibodies can be measured. In addition, a "titer dilution$_{50}$ value" can be determined by using an ELISA (e.g., with one or more immobilized FRα polypeptides) and measuring the optical density (OD) of dilutions (e.g., serial dilutions) of a serum sample from a mammal. The dilution factor that results in a 50 percent reduction from the maximal OD is considered to be the titer dilution$_{50}$ value. This value can be calculated by curve fitting using, for example, the SOFTmax® Pro 4.0 software program that is available from Molecular Devices, Inc. (Sunnyvale, Calif.). Using a four parameter non-linear regression for curve fitting, this program can be used to fit data points to a curve and determine the titer dilution$_{50}$ value. In some cases, PBMCs from a mammal can be analyzed using an ELIspot to detect T cells reactive to FRα polypeptides as described herein. In some cases, an antibody ELISA assay or cytokine flow cytometry can be performed as described herein to assess immunity against a folate receptor polypeptide in a mammal following administration of a composition comprising an FRα polypeptide.

This document also provides methods and materials for identifying a mammal (e.g., a human) as having cancer (e.g., breast or ovarian cancer). For example, a mammal can be identified as having cancer if the level of anti-folate receptor polypeptide antibodies in the mammal (e.g., in a serum sample from the mammal) is an elevated level. If the level of anti-folate receptor polypeptide antibodies in a mammal (e.g., in a serum sample from the mammal) is not an elevated level, then the mammal can be classified as not having cancer.

An anti-folate receptor polypeptide antibody can be any antibody that binds to a folate receptor polypeptide. For example, an anti-folate receptor polypeptide antibody can be an antibody that binds to an FRα polypeptide. In some cases, an anti-folate receptor polypeptide antibody can be an antibody directed against a polypeptide selected from the group consisting of FR5, FR12, FR30, FR56, FR76, FR95, FR113, FR120, FR138, FR147, FR152, FR156, FR225, and FR238. An anti-folate receptor polypeptide antibody can bind to a folate receptor polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$). In addition, an anti-folate receptor polypeptide antibody can be of any type, (e.g., IgG, IgM, IgD, IgA or IgY), class (e.g., IgG1, IgG4, or IgA2), or subclass.

The term "elevated level" as used herein with respect to the level of anti-folate receptor polypeptide antibodies is any level that is greater than a reference level for anti-folate receptor polypeptide antibodies. The term "reference level" as used herein with respect to anti-folate receptor polypeptide antibodies is the level of anti-folate receptor polypeptide antibodies found in mammals free of cancer. For example, a reference level of anti-folate receptor polypeptide antibodies can be the average level of anti-folate receptor polypeptide antibodies that is present in samples obtained from a random sampling of 20 or more (e.g., 30, 40, 50, 60, 70, 80, 90, 100, 200, 300, 400, 500, 600, 700, 800, 900, 100, or more) healthy mammals. It will be appreciated that levels from comparable samples are used when determining whether or not a particular level is an elevated level.

An elevated level of anti-folate receptor polypeptide antibodies can be any level provided that the level is greater than a corresponding reference level for anti-folate receptor polypeptide antibodies. For example, an elevated level of anti-folate receptor polypeptide antibodies can be 0.5, 1, 2, 3, 4, 5, 6, 7, 8, 9, 10, 15, 20, or more times greater than the reference level for anti-folate receptor polypeptide antibodies. In addition, a reference level can be any amount. For example, a reference level for anti-folate receptor polypeptide antibodies can be zero. In this case, any level of anti-folate receptor polypeptide antibodies greater than zero would be an elevated level. In some cases, an elevated level of anti-folate receptor polypeptide antibodies can be a level greater than about 25 ng/mL, 30 ng/mL, 35 ng/mL, 40 ng/mL, 45 ng/mL, 50 ng/mL, 55 ng/mL, or 60 ng/mL.

Any method can be used to determine the level of anti-folate receptor polypeptide antibodies present within a mammal. For example, the level of anti-folate receptor polypeptide antibodies present within a sample from the mammal can be determined using FRα polypeptides provided herein. One or more than one FRα polypeptide can be immobilized on a surface (e.g., the surface of an ELISA plate), non-specific binding can be blocked, and the immobilized polypeptides can be incubated with a sample (e.g., a sample of serum) from a mammal. A labeled antibody that can bind to an anti-folate receptor polypeptide antibody can be used to detect a level of anti-folate receptor polypeptide antibodies bound to the one or more than one FRα polypeptide. An antibody can be labeled directly or indirectly. Suitable labels include, without limitation, radioisotopes (e.g., $^{125}$I, $^{131}$I, $^{35}$S, $^{3}$H, $^{32}$P, $^{33}$P, or $^{14}$C), fluorophores (e.g., fluorescein, fluorescein-5-isothiocyanate (FITC), PerCP, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin and then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multilayer" assays) familiar to those in the art can be used to enhance the sensitivity of assays.

In some cases, a level of anti-folate receptor polypeptide antibodies can be determined in a sample (e.g., a serum sample) from a mammal by exploiting the phenomenon of surface plasmon resonance, which results in a change in the intensity of surface plasmon resonance upon binding that can be detected qualitatively or quantitatively by an appropriate instrument, e.g., a Biacore apparatus (GE Healthcare, United Kingdom). One or more than one FRα polypeptide can be immobilized on the sensor surface of a Biacore apparatus and the immobilized polypeptide can be incubated with a sample (e.g., a diluted serum sample) from a mammal to determine a level of anti-folate receptor polypeptide antibodies. A standard curve using known quantities of anti-folate receptor polypeptide antibodies can be generated to aid in the quantitation of anti-folate receptor polypeptide antibody levels.

Any type of sample can be used to evaluate a level of anti-folate receptor polypeptide antibodies including, without limitation, serum, blood, and plasma. In addition, any method can be used to obtain a sample. For example, a blood sample can be obtained by peripheral venipuncture. Once obtained, a sample can be manipulated prior to measuring the level of anti-folate receptor polypeptide antibodies. For example, a blood sample can be heparanized, centrifuged, or frozen prior to analysis. In addition, replicates and multiple dilutions of a sample can be analyzed.

This document also provides kits that can be used to perform a method provided herein (e.g., to assess immunity against a folate receptor polypeptide in a mammal having cancer). Such kits can include FRα polypeptides, labeled secondary antibodies, control serums (e.g., serums that do or do not contain antibodies directed against, or T cells reactive to, folate receptor polypeptides), ELISA plates, or data analysis software, optionally together with any other appropriate reagent, tool, or instruction for performing a method described herein. Appropriate informational material can be descriptive, instructional, marketing, or other material that relates to the methods described herein and/or the use of the reagents for the methods described herein. For example, the informational material can relate to assessing or increasing immunity against a folate receptor polypeptide in a mammal. In addition, the informational material of a kit can be contact information, e.g., a physical address, e-mail address, website, or telephone number, where a user of the kit can obtain substantive information about analyzing immunity against a folate receptor polypeptide and interpreting the results, particularly as they apply to prognosis of a human having cancer.

The informational material of the kits can be in any form. In many cases, the informational material, e.g., instructions, can be provided in printed matter, e.g., a printed text, drawing, and/or photograph, e.g., a label or printed sheet. Informational material can be provided in other formats, such as Braille, computer readable material, video recording, or audio recording. Informational material can also be provided in any combination of formats.

The kit can include one or more containers for the reagents for assessing or increasing immunity, such as reagents for performing flow cytometry, an ELISA, or any other method described herein. The kit can contain separate containers, dividers, or compartments for the reagents and informational material. A container can be labeled for use for the diagnosis and/or prognosis of a human relating to the development and treatment of cancer.

This document also provides methods and materials to assist medical or research professionals in determining whether or not a mammal has cancer, or in determining whether or not a mammal having cancer has a poor prognosis. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the presence, absence, or level of immunity against a folate receptor polypeptide, and (2) communicating information about the presence, absence, or level to that professional.

Any appropriate method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

The invention will be further described in the following examples, which do not limit the scope of the invention described in the claims.

EXAMPLES

Example 1—Assessing Folate Receptor Immunity

Materials:

Phorbol myristate acetate (PMA), human serum albumin (HSA), polyclonal human IgG, tetanus toxin (TT), and ionomycin were from Sigma (St. Louis, Mo., USA). Goat anti-human horseradish peroxidase (HRP)-conjugated antibody was obtained from Santa Cruz Biotechnology (Santa Cruz, Calif.). FITC-conjugated anti-CD4, PE-conjugated anti-IFN-γ, APC-conjugated anti-CD8, and all cytokine flow cytometry reagents were obtained from BD Biosciences (San Jose, Calif.). Hank's balanced salts solution (HBSS), RPMI-1640 and phosphate-buffered saline were from Cellgro (Hemden, Va., USA). Ficoll-Paque was from Amersham Biosciences (Uppsala, Sweden). The CEF viral polypeptide pool was from the NIH AIDS Research and Reference Reagent Program.

Epitope Prediction and Synthesis:

FRα epitopes were predicted as described elsewhere (Knutson and Disis, *Cancer Immunol. Immunother.*, 54:721-8 (2005)) using RANKPEP (World Wide Web at mifoundation.org) (Table 1, FIG. 1). The sequence for FRα was from the Entrez Database (accession #P15328). Polypeptides were predicted that potentially bound to HLA-DR1, HLA-DR2, HLA-DR3, HLA-DR4, HLA-DR5, HLA-DR7, and HLA-DR11 (Table 1). The algorithm predicted polypeptides of fifteen residues. If a polypeptide was predicted to bind to at least three different HLA-DR alleles, it was selected. In some cases, a polypeptide was extended beyond fifteen residues so that a predicted binding core was flanked by at least three amino acids. The polypeptides, 15-19 residues, were produced to >95% purity by HPLC and mass-spectrometry at the Mayo Clinic. Routine testing of polypeptides demonstrated that they are negative for contamination by splenocyte blastogenesis assays. In select cases, the predicted epitopes were further analyzed using MHCPred (World Wide Web at jenner.ac.uk) for encompassed HLA-A1 (0101), -A2 (0102), and -A3 (0301). These three HLA-A alleles were selected because they are those which are the highest amongst Caucasians, African Americans, and Hispanics. Polypeptides were considered to potentially contain embedded HLA-class I epitopes if the algorithm predicted regions with $IC_{50}$ values of less than or equal to 500 nM. Additionally, FRα-derived T cell epitopes were also analyzed using B cell epitope prediction algorithms ABCpred (www.imtech.res.in) and Antigenic (bioinfo.bgu.ac.il), to determine if they would be useful for detecting antibodies.

Patients and Donors:

Ten healthy donor samples and twenty patient samples were obtained at the Mayo Clinic. Ten patient samples were obtained from the University of Washington (shipped on dry ice) and were processed and stored using the same procedures as the Mayo Clinic samples. Patients were free from active treatment for at least 30 days when blood was drawn. Blood (200 mL) was collected over about a seven month period. The mean (±s.e.m) ages of the healthy donors and patients were 42±11 and 55±2, respectively (p<0.0001). Healthy donors were recruited by means of local advertisement which gave the details of the blood draw. For the antibody ELISA studies, sera was available from eleven healthy controls and nineteen patients.

Peripheral Blood Mononuclear Cell Preparation (PBMC):

An equal volume of Hank's balanced salt solution (HBSS) was added to the blood samples. Twenty-five mL of diluted blood was overlaid onto 15 mL of Ficoll-Paque in a 50 mL conical test tube centrifuged at 374×g for 35 minutes at room temperature. Following centrifugation, the buffy coats were centrifuged (12 minutes, 216×g). The cell pellets were washed and resuspended in freezing media (RPMI supplemented with 12.5% HSA, penicillin, streptomycin, and 2 mM glutamine). Cells were adjusted to $20 \times 10^6$/mL cells, and an equal volume of cold 12.5% HSA RPMI containing 25% DMSO (Sigma D2650) was added. Cells were aliquoted and transferred to a −80° C. freezer. After overnight incubation, the vials were transferred to liquid nitrogen.

For in vitro assay, each vial of cells was thawed, and the contents were transferred to a test tube containing 12 mL of cell culture media. Following centrifugation, the cells were resuspended in 2-3 mL of medium, and viability was determined by dye exclusion. The mean number of PBMC purified from the blood of donors was $1.6 \pm 0.07 \times 10^6$ cells/mL of whole blood for healthy donors and $1.0 \pm 0.07 \times 10^6$/mL for cancer patients (p<0.0001). This cryopreservation and thawing procedure was optimized for recovery of antigen-specific T cell function (Disis et al., *J. Immunol. Methods*, 308(1-2):13-8 (2006)).

IFN-γ ELISpot Analysis:

A 10-day ELIspot for detecting low-frequency T cells was used to determine reactivity to the FRα-derived polypeptides (Table 1). ELIspots were carried out in groups of two donors (two healthy donors, one healthy donor/one cancer patient, or two cancer patients). The assay was carried out as described elsewhere (Knutson et al., *J. Clin. Invest.*, 107: 477-84 (2001)). On day 1, $2.5 \times 10^5$ PBMCs/well were plated into 96-well plates in 3-well replicates in 200 µL of RPMI-1640 containing L-glutamine, penicillin, streptomycin, and 10% fetal calf serum (T-cell medium) in the presence or absence of 10 µg/mL polypeptide antigen. The cells were incubated at 37° C. and IL-2 (Zeptometric, Inc., Buffalo, N.Y.) was added to 10 U/mL on day 5. On day 8, 2.5×10$^5$/well irradiated autologous PBMCs and 10 µg/mL antigens were added. On day 9, the cells were transferred to an anti-IFN-γ-coated nitrocellulose (NC)-plate (Millipore Corporation, Bedford, Mass.). The NC-plate was incubated (37° C.) for a further 20-24 hours followed by washing three times using PBS containing 0.05% Tween-20. The plate was then incubated for 2.5 hours at RT in PBS with 5 µg/mL biotinylated anti-IFN-γ Ab, washed in PBS, and further incubated with 100 µL/well avidin-horseradish peroxidase (HRP, Vector Laboratories, Burlingame, Calif.)) for 2 hours at room temperature. After three washes in PBS, the plate was incubated with 100 µL/well HRP-colorimetric substrate (Vector Laboratories) for 20-30 minutes, rinsed with cool tap water, and allowed to dry completely. The nitrocellulose plates were read on an AID ELIspot reader (Cell Technology, Inc., Columbia, Md.; reader software v.3.1.1.). A positive response was defined as a frequency that was significantly ($p<0.05$, two-tailed t test) greater than the mean of control no-antigen wells and detectable (i.e., >1:100,000). A 17-amino acid polypeptide (KISQAVHAAHAEINEAG; SEQ ID NO: 1) derived from chicken egg ovalbumin, produced in the same fashion as the FRα polypeptides, was used as a control polypeptide. This polypeptide was predicted to bind to HLA-DR2 and DR5 but not DR1, 3, 4, 7, or 11. The anti-IFN-γ and biotinylated anti-IFN-γ antibody pair were obtained from Mabtech (Sweden).

Cytokine Flow Cytometry:

PBMC were cultured with peptide (10 µg/mL) for seven days. IL-2 (20 U/mL) were added on Day 3. After seven days, the cells were distributed into a 96-well plate with fresh irradiated autologous PBMC. Either medium alone or medium supplemented with PHA-L (20 µg/well) or recall polypeptide (10 µg/well) was added to the appropriate wells for 29 hours. Golgi-Stop was added for the last five hours followed by washing in PBS-0.5% BSA. The cells were resuspended in the same buffer containing anti-CD4-FITC and anti-CD8-APC for 30 minutes, followed by washes and fixing. The cells were permeabilized alone or with unconjugated anti-human IFN-γ (adsorption control) followed by washing and incubation with anti-human anti-IFN-γ-APC for 30 minutes. The cells were washed, fixed, and analyzed using a BD Biosciences FACscan flow cytometer and Cell-Quest Pro Software (version 4.0.2., BD Biosciences). A response to antigen was considered as positive if there was at least a 50% increase in IFN-γ☐ cells, and it was blocked by the adsorption control.

Statistics:

The T cell magnitude for each donor was summed across all 14 polypeptides which, along with the response multiplicity, was compared with age using regression. Student's t test was used for means unless the data were not normally

TABLE 1

FRα polypeptides

| SEQUENCE | SEQ ID NO: | POSITIONS | DESIGNATION | LENGTH (AA) | DR1 | DR2 | DR3 | DR4 | DR5 | DR7 | DR11 | # OF HLA |
|---|---|---|---|---|---|---|---|---|---|---|---|---|
| MTTQLLLLLVWVAVVGEAQ | 2 | 5-23 | FR5 | 19 | X | | X | X | | X | X | 5 |
| LLVWVAVVGEAQTRI | 3 | 12-26 | FR12 | 15 | X | | | X | | | X | 3 |
| RTELLNVCMNAKHHKEK | 4 | 30-46 | FR30 | 17 | X | | X | X | | | | 3 |
| QCRPWRKNACCSTNT | 5 | 56-70 | FR56 | 15 | X | | X | X | | | | 3 |
| KDVSYLYRFNWNHCGEMA | 6 | 76-93 | FR76 | 18 | X | X | X | X | X | | X | 6 |
| ACKRHFIQDTCLYECS | 7 | 95-110 | FR95 | 16 | | X | X | | X | | | 3 |
| LGPWIQQVDQSWRKERV | 8 | 113-129 | FR113 | 17 | X | | | X | X | X | X | 5 |
| VDQSWRKERVLNVPL | 9 | 120-134 | FR120 | 15 | X | | X | X | | X | X | 5 |
| DCEQWWEDCRTSYTCK | 10 | 138-153 | FR138 | 16 | | X | | X | | X | | 3 |
| RTSYTCKSNWHKGWNWT | 11 | 147-163 | FR147 | 17 | | | | X | | X | X | 3 |
| CKSNWHKGWNWTSGFN | 12 | 152-167 | FR152 | 16 | X | | | X | X | X | X | 5 |
| WHKGWNWTSGFNKCAVGA | 13 | 156-174 | FR156 | 18 | | X | | X | | | X | 3 |
| VARFYAAAMSGAGPWA | 14 | 225-240 | FR225 | 16 | X | X | | X | | | X | 4 |
| PWAAWPFLLSLALMLLWL | 15 | 238-255 | FR238 | 18 | X | | X | X | | X | X | 5 |

Antibody Enzyme-Linked Immunosorbent Assay (ELISA):

Antigen (10 µg/well) was prepared in 0.06 M carbonate buffer and added to ELISA microtiter plates for 24 hours. Plates were washed with PBS and blocked with 3% BSA-PBS. One hundred microliters of diluted serums (1:125 for polypeptide and 1:40 for tetanus toxoid in 1% BSA-PBS) were added, and the plates were further incubated for 2 hours at room temperature followed by washing with PBS/0.1% Tween-20. A 1:2000 dilution of anti-IgG-HRP was added to wells for 1 hour followed by washing and color development with TMB (3,3',5,5' tetramethylbenzidine substrate was added (100 µL) to the wells. Color development was stopped with 50 µL of a 0.1 N HCl solution. For the standard curve, serial dilutions of human IgG were added to separate wells. As a control, a polypeptide derived from human collagen II, HII.71 (PPGLTGPAGEPGRQGSPGAD; SEQ ID NO:16), was used.

distributed, in which case Mann-Whitney test was used. Fisher's Exact Test was used for comparing proportions. A proportion was considered elevated, relative to other polypeptides, if that proportion was statistically elevated relative to the mean proportion, 8.7%, which is the ratio of the total number of significant ($p<0.05$, two-tailed t test) polypeptide-specific responses over the total number of donors. Tests were performed using InStat (v.3.00), GraphPad Software (San Diego, Calif.). Changes were considered significant if $p<0.05$. Unless specified, one-tailed tests were used. The mean proportion method (Table 2) is used because the ELIspot does not provide a continuous read out due to (1) the limits of detection, and (2) zero value assignment if not significantly different than control. The use of a mean proportion is a rigorous modification of a technique that is used in prior immunologic studies.

TABLE 2

Fisher's Exact Test for Proportion Responding

| Peptide | Healthy Donor Proportion (%) | Patients Proportion (%) | p Value* | p Value** |
|---|---|---|---|---|
| FR5 | 6 | 17 | 0.2 | 0.2 |
| FR12 | 6 | 7 | 0.6 | 0.7 |
| FR30 | 6 | 30 | 0.02 | 0.04 |
| FR56 | 6 | 33 | 0.007 | 0.03 |
| FR76 | 11 | 13 | 0.4 | 0.6 |
| FR95 | 6 | 23 | 0.07 | 0.1 |
| FR113 | 0 | 27 | 0.03 | 0.02 |
| FR120 | 11 | 13 | 0.4 | 0.6 |
| FR138 | 22 | 30 | 0.02 | 0.4 |
| FR147 | 22 | 40 | 0.001 | 0.2 |
| FR152 | 6 | 23 | 0.07 | 0.1 |
| FR156 | 17 | 23 | 0.07 | 0.4 |
| FR225 | 22 | 7 | 0.6 | 0.1 |
| FR238 | 0 | 23 | 0.07 | 0.03 |

*Fisher's Exact Test (one-tailed) comparing if the proportion of patients responding to polypeptide is higher than the mean proportion of 8.7%.
**Fisher's Exact Test comparing if the proportion of patients is higher than the proportion of healthy individuals responding to polypeptide.
Those comparisons deemed statistically significant are bolded.

Patients with Breast and Ovarian Cancer Generate Immunity to Multiple Polypeptide Epitopes in FRα.

Figure 3A:
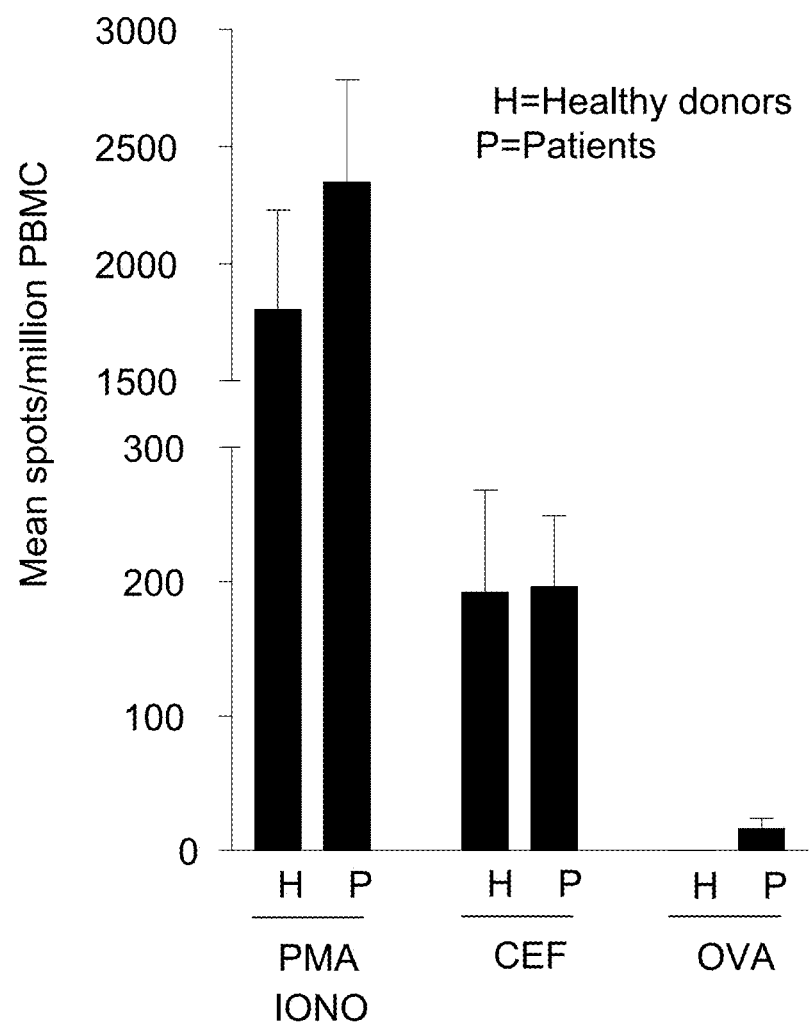
Figure 3B:
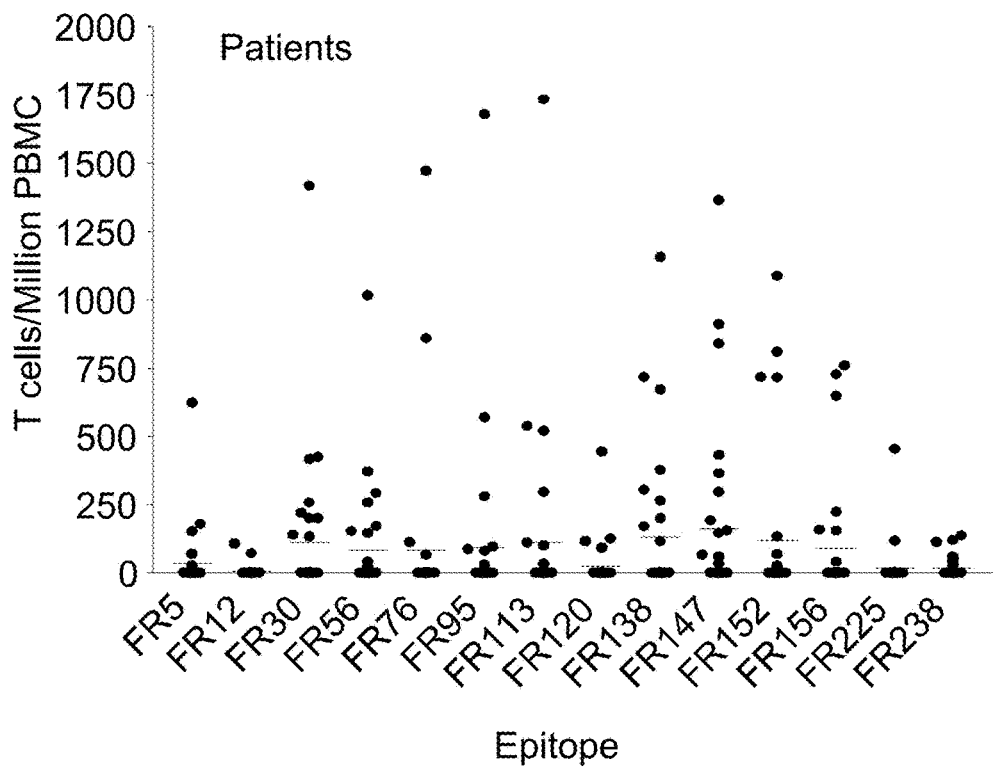
Figure 3C:
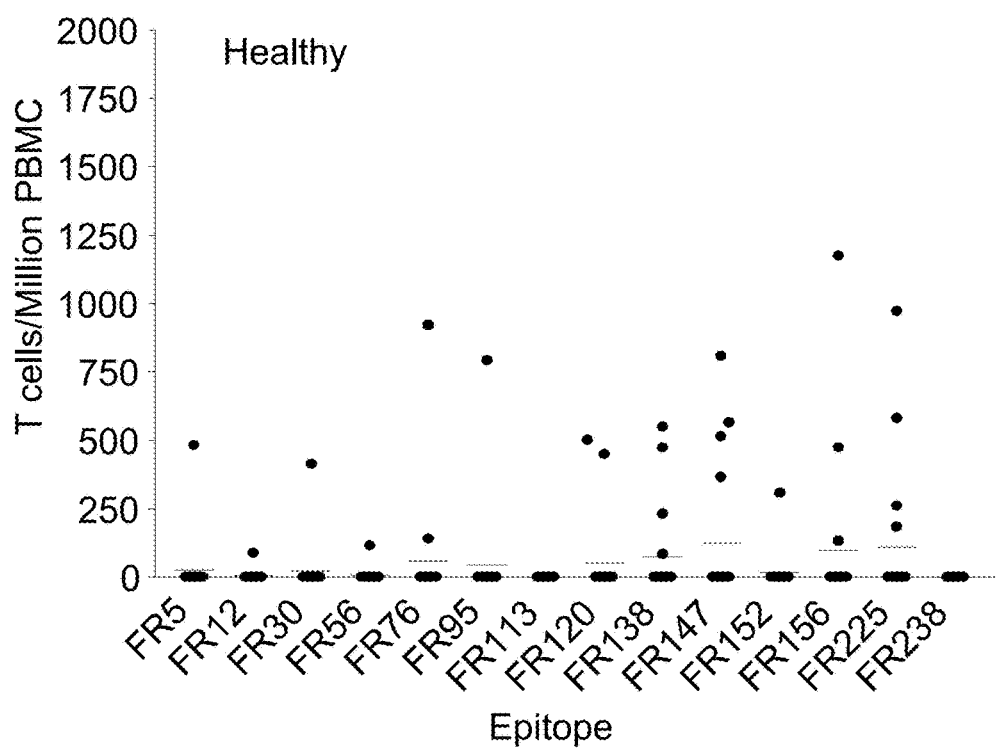
Figure 3D:
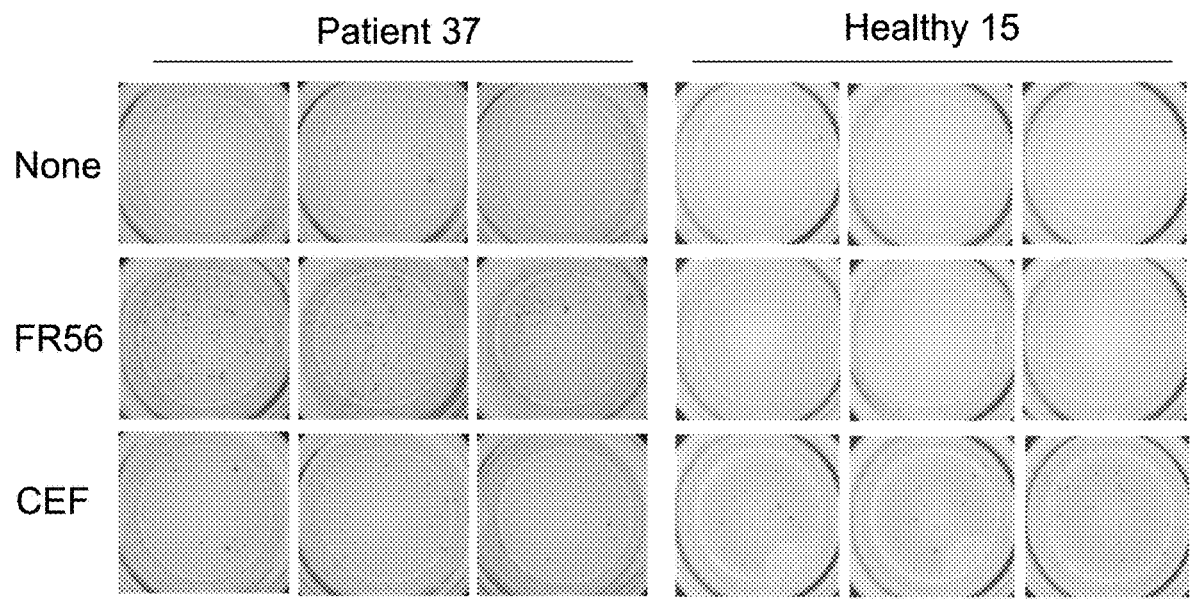
Figure 3E:
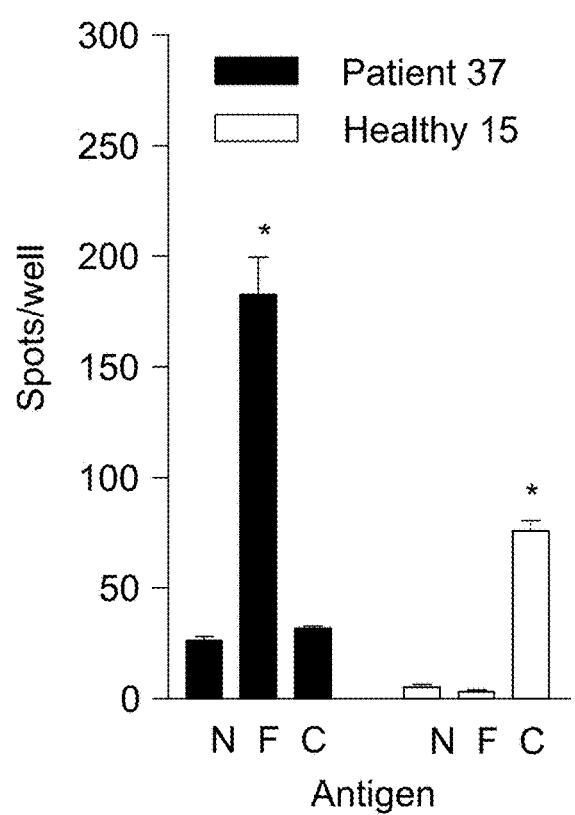

The FRα polypeptides predicted to be immunogenic were distributed throughout the receptor (FIG. 1). Responses to PMA/ionomycin, the CEF polypeptide pool, and an ovalbumin-derived control polypeptide were not different between the two populations (FIG. 3A). T cell frequencies were determined for each of the FRα polypeptides for the patients (FIG. 3B) and the healthy donors (FIG. 3C). The mean frequencies for each of the polypeptides ranged from 0-124 T cells/million PBMC for the normals and 1-162/million PBMC for the patients. The overall mean FRα-specific T cell frequency, considering all polypeptides, for patients was 74±11 (mean±s.e.m., n=448) and for healthy donors was 46±10 (n=226) (p=0.05). An ELIspot for patient 37 and healthy donor 15 was performed (FIGS. 3D-E). Patient 37 demonstrated an FR56-specific response (183±17 spots/well, mean±s.e.m., n=3) which was higher (p=0.0008) than no antigen (26±2 spots/well) control. The responses to the CEF pool were not significantly elevated compared to control (p>0.5). Donor 15 did not demonstrate elevated FR56-specific T cell (3±1 spots/well, p>0.05) compared to control (5±1 spots/well), but did have an elevated CEF pool response (76±5 spots/well, p=0.0003).

Both CD4+ and CD8+ T cells were activated in response to the polypeptide stimulation. PBMC from three patients that had responded to FR56 were examined using IFN-γ cytokine flow cytometry. Analysis of the FR56 polypeptide using the MHCPred MHC class I predicting algorithm suggested this epitope contained high affinity binding epitopes for HLA-A2 and HLA-A3. All three patients demonstrated a CD4 T cell response to the FR56 polypeptide while two of three demonstrated a CD8 T cell response of which a representative example is shown in FIGS. 3F-I.

Figure 3J:
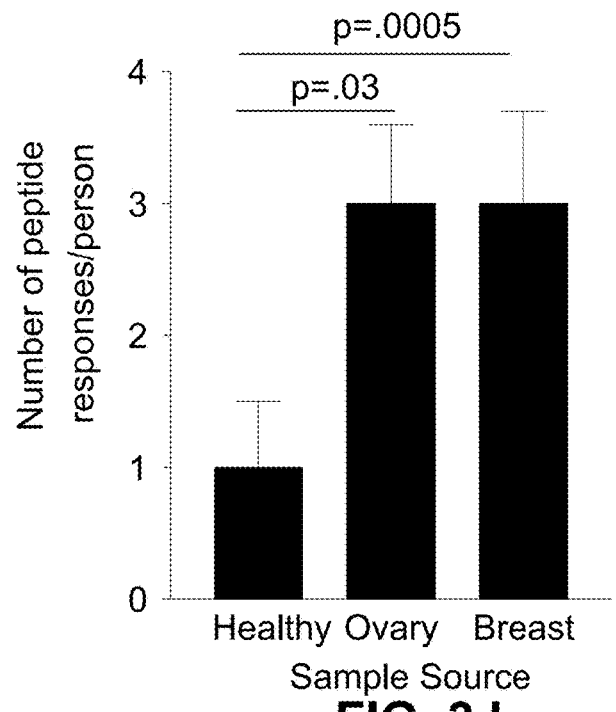
Figure 3K:
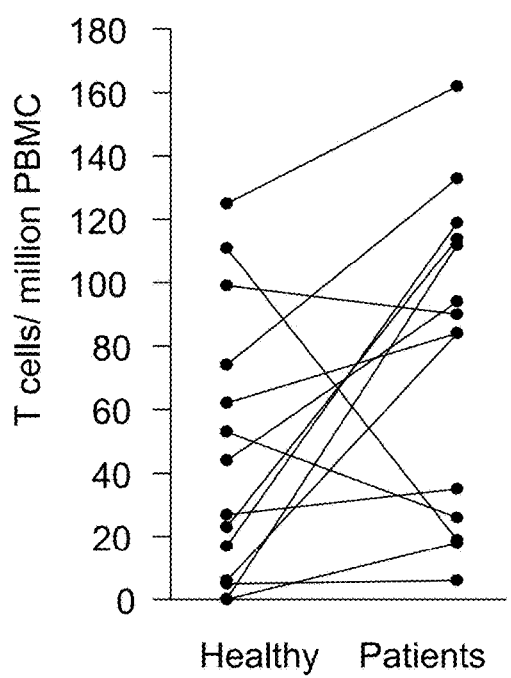
Figure 3L:
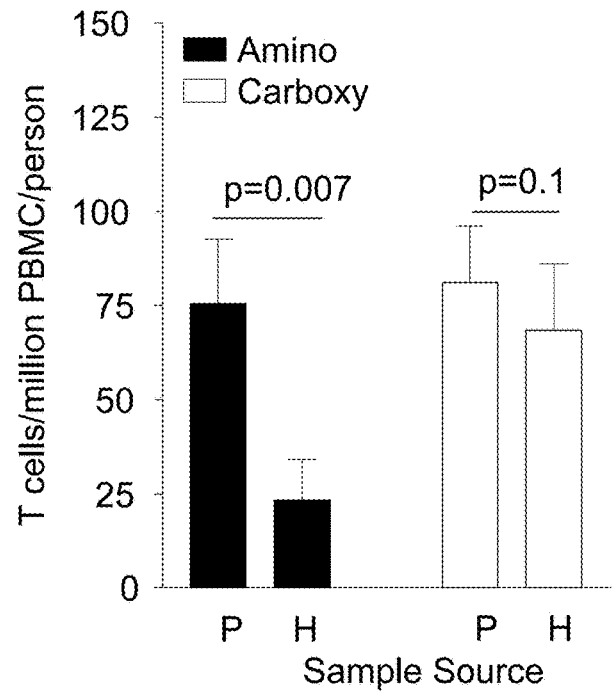

It was observed that ovarian and breast cancer patients demonstrated immunity to 3±0.6 (mean±s.e.m.) and 3±0.7 FRα-derived polypeptides, respectively (FIG. 3J). These levels of reactivity were higher than healthy donors who responded to 1±0.5 (n=18) polypeptides. As shown in the relational diagram (FIG. 3K), the calculated frequency of eleven of the polypeptides was increased in patients while three were similar or decreased. The elevated T cell frequencies observed in the patient were mostly confined to the amino terminus as shown in FIG. 3L. The mean T cell frequency per patient for the amino terminus polypeptides was 75±17 (mean±s.e.m) which was higher than the frequency observed in healthy donors (24±11, p=0.007). There was no difference in the mean T cell precursor frequencies to the carboxy polypeptides (p=0.1). Further, there were no associations between the T cell frequencies and the number of HLA-DR alleles to which each polypeptide was predicted to bind. There were no effects of age (range 25-73) on either the numbers of polypeptides that elicited an immunogenic response ($r^2$=0.006, p=0.6, 2-tailed) or the magnitude of the T cell responses ($r^2$=0.004, p=0.7).

A High Proportion of Breast and Ovarian Cancer Patients have T Cell Responses to FRα.

Figure 2A:
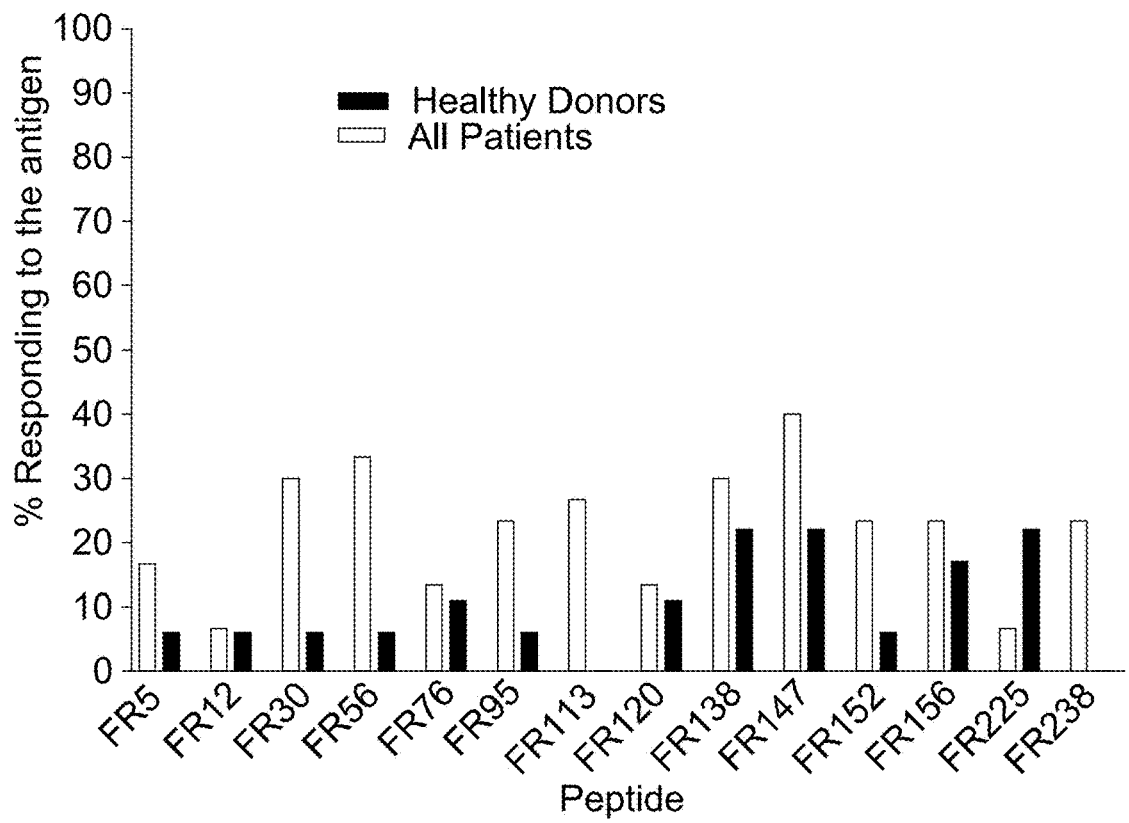
FIGS. 2A-2C contain three bar graphs demonstrating that a high proportion of breast and ovarian cancer patients have T cell responses to an FRα polypeptide. Panel A is a bar graph plotting the proportions of healthy donors and patients responding to the indicated polypeptide epitopes. Panel B is a bar graph plotting the proportions of both ovarian and breast cancer patients that responded to the indicated polypeptide epitopes. Panel C is a bar graph plotting the distribution of responses amongst either the amino terminus half (Amino) or the carboxy terminus half (Carboxy) of an FRα polypeptide in both patients and healthy donors.
Figure 2B:
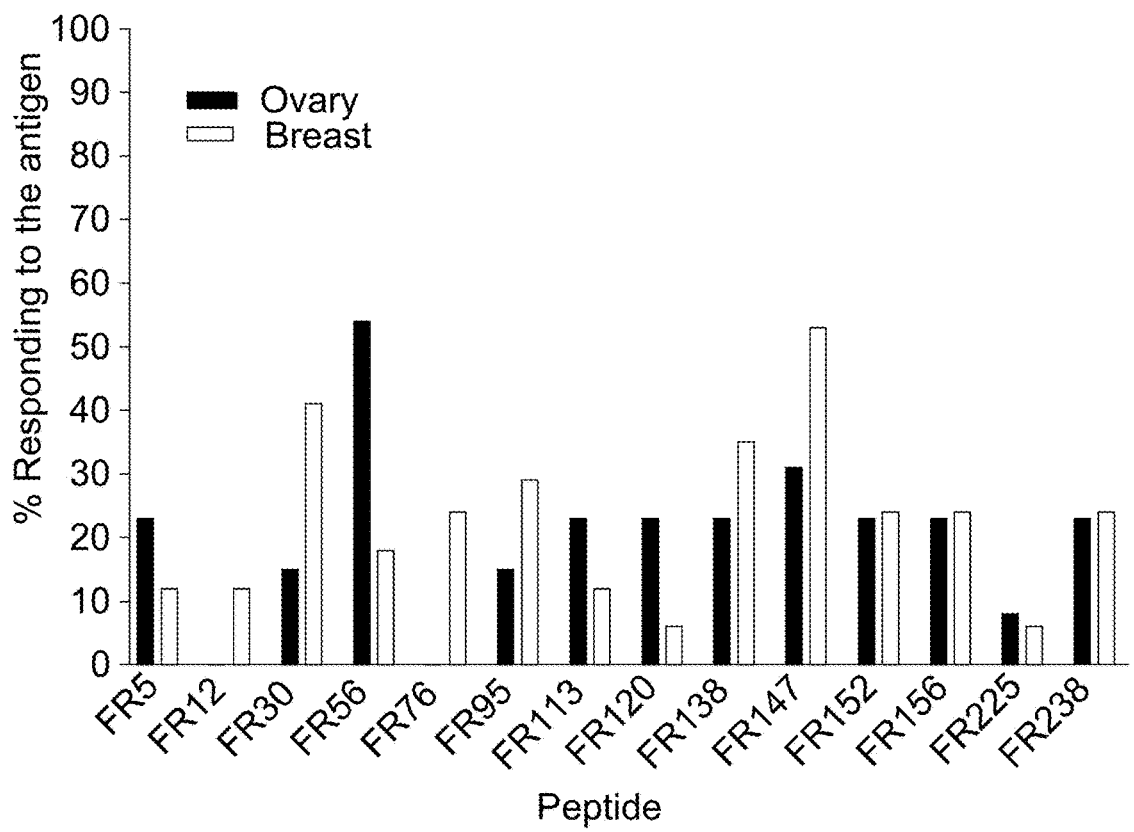

The percentage of patients who responded to each polypeptide was determined and found to range from 7-40% (FIG. 2A). Patients responded in higher proportions (p<0.05) to FR30 (30%), FR56 (33%), FR113 (27%), FR138 (30%), and FR147 (40%) (Table 2). Responses were more frequently observed in cancer patients than in healthy donors. Of the 14 polypeptides, four (FR30, FR56, FR113, FR238) generated responses in more patients than healthy donor counterparts (Table 2). Reactivity to three of these, FR30, FR56, and FR113, was observed in greater than 25% of patients. Of the fourteen FRα polypeptides, FR56 was recognized more often (p=0.05) by ovarian cancer patients than by breast cancer patients (FIG. 2B). Overall, 69% and 76% of ovarian and breast cancer patients, respectively, demonstrate immunity to at least one eptiope of FRα.

Figure 2C:
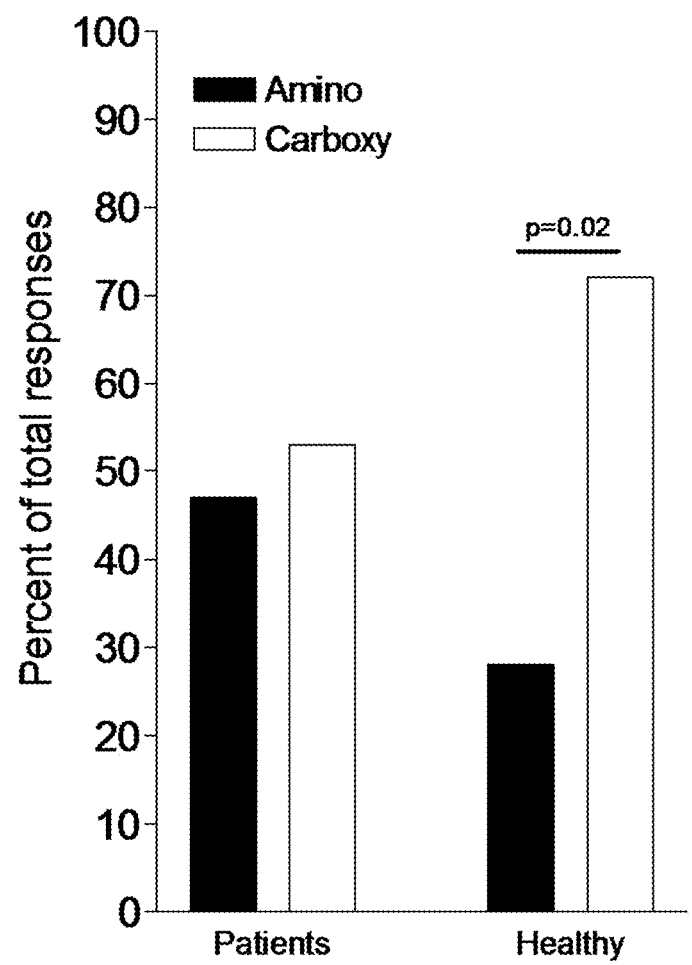

The responses in the patients were equally distributed amongst the amino terminus polypeptides (FR5-FR113) and the carboxy terminus polypeptides (FR120-FR238). 47% and 53% of the polypeptide responses were directed toward the amino and carboxy terminus polypeptides, respectively (p=0.5; FIG. 2C). The responses observed in normal control individuals were more frequently observed in the carboxy terminus (72%) compared to the amino terminus (28%).

Breast and Ovarian Cancer Patients Demonstrate FRα-Specific Antibody Immunity.

Figure 4A:
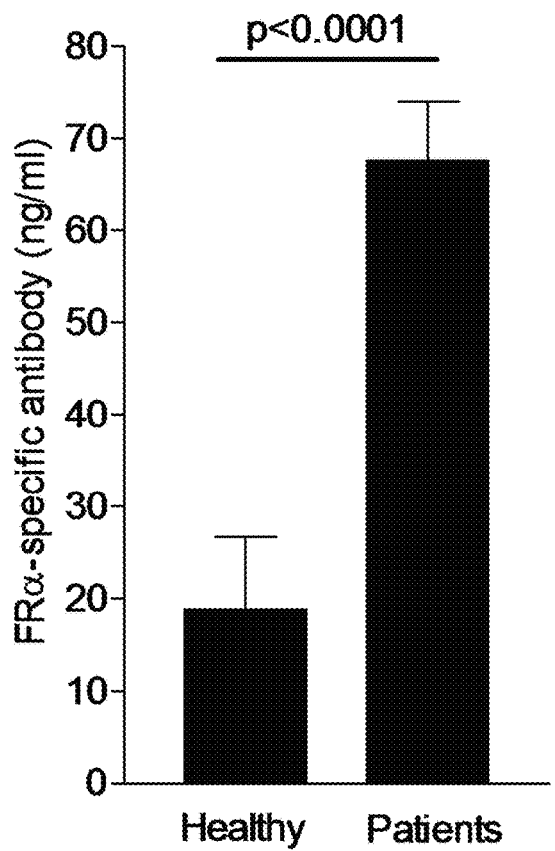
FIGS. 4A-4B.
Figure 4B:
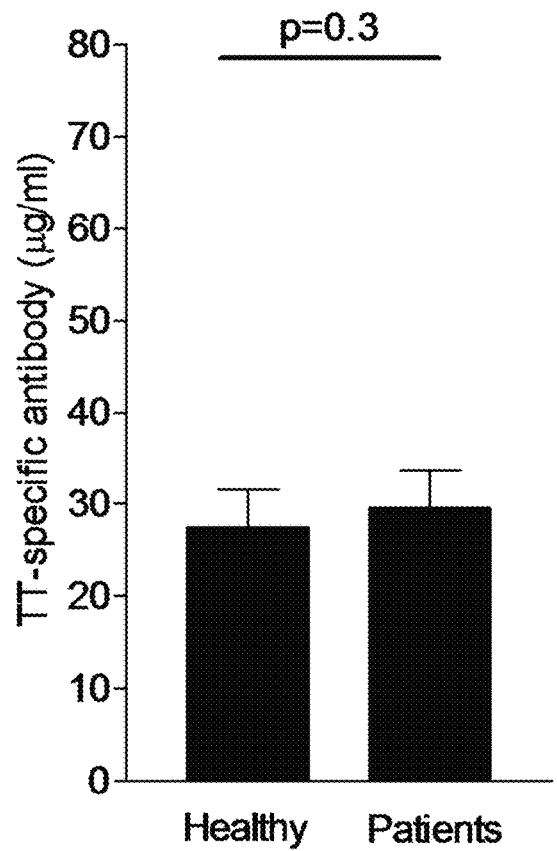

Patients demonstrated increased antibody immunity to FRα (FIG. 4A). Levels of FRα-specific antibodies in patients were 68±6 ng/mL (mean±s.e.m., n=18), which was significantly higher (p<0.0001) than levels in the normal healthy donors (19±8 ng/ml, n=1). Antibody responses to TT were equivalent (p=0.3) between the 2 populations (patients, 30±4 µg/mL; healthy donors 27±4 µg/mL, p=0.3; FIG. 4B).

The detection of pre-existent immunity to cancer antigens is useful because it identifies antigens to which tolerance induction by the host is nonexistent, incomplete or reversible. Furthermore, this immunity can indicate that a patient's immune system may have responded to the tumor and is potentially involved in tumor rejection. These antigens could be targeted with immune-based cancer treatment and prevention strategies such as cancer vaccines as it may be easier to expand a memory pool of T cells as compared to generating new immunity. As described herein, an MHC class II algorithm was used to define immunogenic regions of the FRα, and FRα-specific immunity was found to be prevalent in patients with breast or ovarian cancer. Of the 14 putative MHC class II polypeptides identified, five polypeptides were recognized by greater than 25% of patients. The response proportion to three of these polypeptides was higher than that observed in a healthy volunteer donor population. Overall, patients responded to an average of three FRα-derived polypeptides suggesting a multi-epitope response whereas the healthy donors responded to one polypeptide and at a lower T cell frequency. Lastly, immunity to the FRα in cancer patients targeted both the amino and carboxy-terminal halves of the molecule whereas immunity observed in healthy donors largely targeted the carboxy terminal half. Collectively, these results demonstrate that tolerance to the FRα is minimal and the majority of patients have immunity to multiple epitopes.

The results provided herein demonstrate that immunity to FRα is prevalent in breast and ovarian cancer patients. Immunity to tumor antigens is typically thought to be very low or undetectable for breast and ovarian cancer. However, this understanding is limited by the capabilities of assessing the tumor-specific immune response which, like infectious disease responses, consists of multiple effectors including CD8⁺ T cells, CD4⁺ T cells, and antibodies. Knowledge of the extent and prevalence of tumor antigen-specific immunity can be used to identify which antigens are naturally targeted by the immune system and to understand why natural immunity fails to eradicate tumors. Several mechanisms are proposed to explain immune escape.

The results provided herein also demonstrate that patients can generate immunity to multiple epitopes suggesting that tolerance to FRα is absent (i.e., immunologic ignorance) or reversible (i.e., anergy). The results demonstrate the existence of multi-epitope FRα-specific immune responses, suggesting that the T cell receptor repertoire targeting FRα is largely intact and is maintained in normal healthy individuals by either ignorance or anergy. This is likely due to the fact that in humans expression of FRα is limited to a few tissues, mainly kidney tubules. The observation that patients with breast and ovarian cancer apparently augmented immunity to the FRα, particularly to epitopes in the amino terminal half of the molecule, shows that the immune system maintains a diverse T cell repertoire that can be expanded in vivo.

Although the polypeptides used herein were predicted CD4⁺ T cell epitopes, results suggest that some responses were due to CD8⁺ T cells that were potentially activated by encompassed MHC class I polypeptides such as with polypeptide FR56. In addition, one of the fourteen polypeptides fully contained an HLA-A2-restricted epitope. That polypeptide, FR238, fully encompasses the HLA-A2 motif, FRα 245-253. In the current study, 23% of patients were found to respond to FR238 while none of the healthy donors responded. Thus, although HLA-A2 expression was not examined, the possibility exists that the patients were responding to the embedded HLA-A2-restricted epitope.

The analyses provided herein suggest that the polypeptides may encompass epitopes that bind to other MHC class I molecules as well (e.g. HLA-A3). Polypeptides that could generate both CD4⁺ and CD8⁺ T cells are useful for generating an effective anti-tumor immune response since several studies have shown that activating both T cell subsets may be better than activating either alone. Coupled with detection of FRα-specific antibodies, the presence of both CD4⁺ and CD8⁺ T cell immunity indicates that a coordinated immune response is being elicited in cancer patients, but that the response may be limited.

The FRα is a tumor-associated antigen that may have a role in the biology of cancer which may explain why it is maintained in a high proportion of tumors. For example, decreasing FRα expression in breast cancer cell lines reduces their proliferation rate. In addition, its high frequency of expression in ovarian cancer (>90%) suggests that FRα confers a growth advantage over tumor cells with reduced expression. Coupled with the observations that the T cell repertoire is intact, these findings suggest that targeting the FRα using immune-based approaches such as cancer vaccines may be advantageous because the immune system would target the most aggressive tumor cells. Targeting antigens that are involved in the biology of the disease may reduce the risks of outgrowth of antigen-negative variants.

In summary, the results provided herein demonstrate that immunity to FRα is prevalent in patients with breast and ovarian cancer. Understanding immunity to tumor-associated antigens should lead to a better understanding of how tumors interact and escape natural immunity. Furthermore, discovery of the epitopes of a tumor antigen such as the FRα could lead to design and testing of strategies to augment tumor-specific immunity.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing folate receptor α (FRα) immunity in a mammal, said method comprising administering a composition to said mammal under conditions effective to increase said FRα immunity, wherein said composition comprises a polypeptide, wherein the amino acid sequence of said polypeptide is as set forth in SEQ ID NO:2.

2. The method of claim 1, wherein said mammal is a human.

3. The method of claim 1, wherein said composition comprises an adjuvant.

4. The method of claim 1, wherein said composition comprises 500 µg of said polypeptide.

5. The method of claim 1, wherein said polypeptide comprises a lipid soluble alkyl.

* * * * *